United States Patent
Stolen et al.

(10) Patent No.: US 11,207,520 B2
(45) Date of Patent: Dec. 28, 2021

(54) SYSTEM AND METHOD FOR CONTROLLING BLOOD PRESSURE

(71) Applicants: Regents of the University of Minnesota, Minneapolis, MN (US); Boston Scientific Scimed, Inc., Maple Grove, MN (US)

(72) Inventors: Craig Stolen, New Brighton, MN (US); Bryan Allen Clark, Forest Lake, MN (US); Manda L. Keller-Ross, Saint Paul, MN (US); Ninitha Margret Julfiya Asirvatham-Jeyaraj, Minneapolis, MN (US); Daniel P. Chantigian, Minneapolis, MN (US)

(73) Assignees: Regents of the University of Minnesota, Minneapolis, MN (US); Boston Scientific Scimed, Inc., Maple Grove, MN (US)

( * ) Notice: Subject to any disclaimer, the term of this patent is extended or adjusted under 35 U.S.C. 154(b) by 257 days.

(21) Appl. No.: 16/414,869

(22) Filed: May 17, 2019

(65) Prior Publication Data
US 2019/0351234 A1 Nov. 21, 2019

Related U.S. Application Data

(60) Provisional application No. 62/673,017, filed on May 17, 2018.

(51) Int. Cl.
*A61N 1/36* (2006.01)
*A61B 5/021* (2006.01)
(Continued)

(52) U.S. Cl.
CPC .......... *A61N 1/36117* (2013.01); *A61B 5/021* (2013.01); *A61B 5/1116* (2013.01);
(Continued)

(58) Field of Classification Search
CPC .................. A61N 1/36117; A61N 1/0551
See application file for complete search history.

(56) References Cited

U.S. PATENT DOCUMENTS

| | | |
|---|---|---|
| 5,507,784 A | 4/1996 | Hill et al. |
| 7,643,875 B2 | 1/2010 | Hiel, Jr. et al. |

(Continued)

FOREIGN PATENT DOCUMENTS

| | | |
|---|---|---|
| EP | 3320949 A1 | 5/2018 |
| WO | WO-2019222619 A1 | 11/2019 |

OTHER PUBLICATIONS

"International Application Serial No. PCT/US2019/032856, International Preliminary Report on Patentability dated Nov. 26, 2020", 8 pgs.

(Continued)

*Primary Examiner* — William J Levicky
*Assistant Examiner* — Naveed R. Kolia
(74) *Attorney, Agent, or Firm* — Schwegman Lundberg & Woessner, P.A.

(57) ABSTRACT

An example of a system includes a blood pressure modulation device and a controller. The blood pressure modulation device may be configured to deliver a therapy to chronically maintain blood pressure within a prescribed range. The blood pressure modulation device may include a neuromodulator configured to deliver neuromodulation energy to neural tissue in a spinal cord or near the spinal cord using a first parameter set. The controller may include analyzer circuitry configured to determine an actual or anticipated blood pressure demand event indicated for a blood pressure change, and therapy parameter adjuster circuitry configured to respond to the actual or anticipated (Continued)

blood pressure demand event by delivering neuromodulation energy using a second parameter set to change the blood pressure.

20 Claims, 8 Drawing Sheets

(51) Int. Cl.
    *A61B 5/11*     (2006.01)
    *A61B 5/00*     (2006.01)
    *A61N 1/05*     (2006.01)
    *A61N 1/372*     (2006.01)

(52) U.S. Cl.
    CPC .......... *A61B 5/1118* (2013.01); *A61B 5/7275* (2013.01); *A61N 1/0551* (2013.01); *A61N 1/36062* (2017.08); *A61N 1/36071* (2013.01); *A61N 1/36139* (2013.01); *A61N 1/36171* (2013.01); *A61N 1/36175* (2013.01); *A61N 1/36178* (2013.01); *A61N 1/36196* (2013.01); *A61N 1/37247* (2013.01)

(56) References Cited

U.S. PATENT DOCUMENTS

| | | | |
|---|---|---|---|
| 8,086,314 | B1 | 12/2011 | Kieval |
| 2007/0073356 | A1* | 3/2007 | Rooney ................. A61N 1/375 607/46 |
| 2013/0289650 | A1* | 10/2013 | Karlsson ............ A61N 1/36117 607/44 |
| 2018/0028824 | A1 | 2/2018 | Pivonka et al. |
| 2018/0071525 | A1 | 3/2018 | Ahmed |
| 2019/0009094 | A1* | 1/2019 | Zhang ................ A61N 1/37247 |

OTHER PUBLICATIONS

"International Application Serial No. PCT/US2019/032856, International Search Report dated Sep. 19, 2019", 5 pgs.
"International Application Serial No. PCT/US2019/032856, Written Opinion dated Sep. 19, 2019", 8 pgs.

* cited by examiner

SYSTEM AND METHOD FOR CONTROLLING BLOOD PRESSURE

CLAIM OF PRIORITY

This application claims the benefit of priority under 35 U.S.C. § 119(e) of U.S. Provisional Patent Application Ser. No. 62/673,017, filed on May 17, 2018, which is herein incorporated by reference in its entirety.

TECHNICAL FIELD

This document relates generally to medical devices and more particularly to a system for device-based system and method for controlling blood pressure.

BACKGROUND

Hypertension, or high blood pressure, affects millions of Americans and is known to be the strongest risk factor for developing cardiovascular disease. Chronic hypertension can lead to cardiac remodeling due to increased load on a patient's heart and can increase the patient's risk of developing heart failure. For about 20-30% of hypertensive patients, common pharmaceutical approaches are unable to control the rise in arterial blood pressure. For these patients, a device-based approach can be used to control blood pressure. One approach for reducing blood pressure is to target the imbalance in the autonomic nervous system often seen in hypertensive patients. This imbalance manifests as an over activation of the sympathetic nervous system and a withdrawal of the parasympathetic nervous system.

Acute blood pressure changes may occur for various reasons. For example, muscle activation such as during postural change or exercise can cause increased sympathetic activity, thereby elevating the blood pressure. Exercise pressor reflex (neurological reflex that constricts arterioles during exercise) may raise the systolic blood pressure of a hypertensive patient to over 200 mmHg. This differs from chronic hypertension, which is marked by baseline systolic blood pressure levels above 140 mmHg. The exercise pressor reflex is particularly problematic for patients who would use exercise to improve their blood pressure. These large spikes in blood pressure can result in cardiovascular, cerebrovascular, and/or organ damage. Proper treatment requires the ability to adapt as activity levels and blood pressure fluctuates. Research into this mechanism has been conducted using fentanyl injections, which blocks sympathetic afferent nerves in the spinal cord to reduce blood pressure during exercise in heart failure patients.

In a hypertensive patient, a persistent increase in blood pressure can result in desensitization of arterial baroreceptors, which can lead to development of orthostatic hypotension. The patient experiences hypertension while in a supine position, but has orthostatic intolerance during a postural transition. This makes the treatment challenging because treating one condition could worsen the other. Such patients can benefit from a treatment option that can reduce blood pressure in a hypertensive state and increase blood pressure when the patient becomes hypotensive, such as during postural changes. For example, a therapy that reduces hypertension can be enabled during the hypertensive state and inhibited during the hypotensive state, or a therapy that heightens the blood pressure can be delivered during the hypotensive state.

A feature of hypertension is abnormally high activity of the sympathetic nervous system. Mechanically- and metabolically-sensitive receptors (group III/IV skeletal muscle afferents) activate during exercise to increase sympathetic activity and subsequently blood pressure (BP). Group III/IV afferent activity is exaggerated in adults with hypertension which causes aberrant elevations in BP during exercise.

Occlusion during exercise and post exercise increases group III/IV afferent activity resulting in greater BP. Putative mechanisms of SCS involve 1) blunting sympathetic activity via modulation of al-adrenergic receptor activity and/or 2) increasing vasodilation via transient receptor potential vanilloid 1 (TRPV1) nerve endings on the group III/IV afferents.

Improvements are needed to reduce blood pressure in adults with hypertension.

SUMMARY

An example (e.g. Example 1) of a system includes a blood pressure modulation device and a controller. The blood pressure modulation device may be configured to deliver a therapy to chronically maintain blood pressure within a prescribed range. The blood pressure modulation device may include a neuromodulator configured to deliver neuromodulation energy to neural tissue in a spinal cord or near the spinal cord using a first parameter set. The controller may include analyzer circuitry configured to determine an actual or anticipated blood pressure demand event indicated for a blood pressure change, and therapy parameter adjuster circuitry configured to respond to the actual or anticipated blood pressure demand event by delivering neuromodulation energy using a second parameter set to change the blood pressure.

In Example 2, the subject matter of Example 1 may optionally be configured such that the neuromodulator includes an electrode array configured to be epidurally implanted proximate to the T10-T12 region for use in delivering the neuromodulation energy to the neural tissue.

In Example 3, the subject matter of any one or any combination of Examples 1-2 may optionally be configured such that the neuromodulator is configured to deliver spinal cord stimulation (SCS) to cause paresthesia.

In Example 4, the subject matter of any one or any combination of Examples 1-3 may optionally be configured such that the neuromodulator is configured to deliver spinal cord stimulation (SC S) that a patient perceives as substantially uniformly distributed in legs of the patient.

In Example 5, the subject matter of any one or any combination of Examples 1-4 may optionally be configured such that the neuromodulation energy delivered using the first parameter set has a lower frequency than the neuromodulation energy delivered using the second parameter set.

In Example 6, the subject matter of any one or any combination of Examples 1-5 may optionally be configured such that the frequency of the neuromodulation energy delivered using the first parameter set is below 500 Hz, and the frequency of the neuromodulation energy delivered using the second parameter set is above 500 Hz.

In Example 7, the subject matter of any one or any combination of Examples 1-6 may optionally be configured such that the frequency of the neuromodulation energy delivered using the first parameter set is within a range between 20 Hz to 200 Hz, and the frequency of the neuromodulation energy delivered using the second parameter set is within a range between 700 Hz to 1500 Hz.

In Example 8, the subject matter of any one or any combination of Examples 1-7 may optionally be configured such that the neuromodulation energy delivered using the first parameter set and the neuromodulation energy delivered using the second parameter set have different waveforms with different pulse patterns.

In Example 9, the subject matter of any one or any combination of Examples 1-8 may optionally be configured such that the neuromodulation energy delivered using the first parameter set and the neuromodulation energy delivered using the second parameter set have different waveforms with different waveform shapes.

In Example 10, the subject matter of any one or any combination of Examples 1-8 may optionally be configured such that the first parameter set and the second parameter set include a different parameter value or a different range of parameter values for at least one parameter selected from the group of parameter consisting of: frequency, pulse width, or burst duration for a burst of pulses.

In Example 11, the subject matter of any one or any combination of Examples 1-10 may optionally be configured such that the first parameter set and the second parameter set include different active electrodes or different fractionalization values for active electrodes.

In Example 12, the subject matter of any one or any combination of Examples 1-11 may optionally be configured such that the blood pressure demand event includes a posture change or an activity change for the patient.

In Example 13, the subject matter of any one or any combination of Examples 1-12 may optionally be configured such that the blood pressure demand event includes at least one of acute decompensation in heart failure, arrhythmia, bradycardia, neurally-mediated hypotension, decreases in blood volume, anaphylactic shock or medication intake.

In Example 14, the subject matter of any one or any combination of Examples 1-13 may optionally be configured such that the analyzer circuitry is configured to determine the actual or anticipated blood pressure demand event using sensed blood pressure or sensed evoked compound action potentials associated with a blood pressure response.

In Example 15, the subject matter of any one or any combination of Examples 1-14 may optionally be configured such that the analyzer circuitry is configured to determine the actual or anticipated blood pressure demand event using sensed activity, sensed posture, or a user-inputted signal.

An example (e.g. Example 16) of a non-transitory machine-readable medium including instructions, which when executed by a machine, cause the machine to deliver a therapy for chronically maintaining blood pressure with a prescribed range, including deliver neuromodulation energy to neural tissue in a spinal cord or near the spinal cord using a first parameter set, determine an actual or anticipated blood pressure demand event indicated for a blood pressure change, and respond to the determined actual or anticipated blood pressure demand event by delivering neuromodulation energy using a second parameter set to change the blood pressure.

In Example 17, the subject matter of Example 1 may optionally be configured such that the therapy includes spinal cord stimulation (SCS) delivered to the T10-T12 region to cause paresthesia in legs of the patient.

In Example 18, the subject matter of any one or any combination of Examples 16-17 may optionally be configured such that the frequency of the neuromodulation energy delivered using the first parameter set is below 500 Hz, and the frequency of the neuromodulation energy delivered using the second parameter set is above 500 Hz.

In Example 19, the subject matter of any one or any combination of Examples 16-18 may optionally be configured such that the actual or anticipated blood pressure demand event is determined using sensed activity, sensed posture, or a user-inputted signal.

In Example 20, the subject matter of any one or any combination of Examples 16-19 may optionally be configured such that the neuromodulation energy delivered using the first parameter set and the neuromodulation energy delivered using the second parameter set have different waveform with different pulse patterns or waveform shapes.

An example (e.g. Example 21) of a method for controlling blood pressure in a patient, includes: delivering a therapy for chronically maintaining blood pressure with a prescribed range, including delivering neuromodulation energy to neural tissue in a spinal cord or near the spinal cord using a first parameter set; determining an actual or anticipated blood pressure demand event indicated for a blood pressure change; and responding to the determined actual or anticipated blood pressure demand event by delivering neuromodulation energy using a second parameter set to change the blood pressure.

In Example 22, the subject matter of Example 21 may optionally be configured such that the blood pressure demand event is indicated for an increased blood pressure.

In Example 23, the subject matter of any one or any combination of Examples 21-22 may optionally be configured such that delivering the therapy includes delivering spinal cord stimulation (SCS) to a thoracic region of the spinal cord.

In Example 24, the subject matter of any one or any combination of Examples 21-23 may optionally be configured such that delivering the SCS includes delivering the SCS within the T10-T12 region.

In Example 25, the subject matter of any one or any combination of Examples 21-24 may optionally be configured such that delivering the SCS includes delivering the SCS to cause paresthesia in legs of the patient.

In Example 26, the subject matter of any one or any combination of Examples 21-25 may optionally be configured such that the paresthesia covers a majority of both legs and is perceived by the patient as substantially uniformly distributed in the legs.

In Example 27, the subject matter of any one or any combination of Examples 21-26 may optionally be configured such that the neuromodulation energy delivered using the first parameter set has a lower frequency than the neuromodulation energy delivered using the second parameter set.

In Example 28, the subject matter of Example 27 may optionally be configured such that the frequency of the neuromodulation energy delivered using the first parameter set is below 500 Hz, and the frequency of the neuromodulation energy delivered using the second parameter set is above 500 Hz.

In Example 29, the subject matter of Example 28 may optionally be configured such that the frequency of the neuromodulation energy delivered using the first parameter set is within a range between 20 Hz to 200 Hz, and the frequency of the neuromodulation energy delivered using the second parameter set is within a range between 700 Hz to 1500 Hz.

In Example 30, the subject matter of any one or any combination of Examples 21-29 may optionally be configured such that the neuromodulation energy delivered using the first parameter set and the neuromodulation energy delivered using the second parameter set have different waveform with different pulse patterns or waveform shapes.

In Example 31, the subject matter of any one or any combination of Examples 21-30 may optionally be configured such that delivering the therapy includes delivering neuromodulation energy to a dorsal column or to a dorsal horn.

In Example 32, the subject matter of any one or any combination of Examples 21-31 may optionally be configured such that delivering the therapy includes delivering neuromodulation energy to a dorsal root ganglia (DRG) or to a dorsal root.

In Example 33, the subject matter of any one or any combination of Examples 21-32 may optionally be configured such that delivering the therapy includes delivering neuromodulation energy to a sympathetic chain or to a peripheral sympathetic nerve.

In Example 34, the subject matter of any one or any combination of Examples 21-33 may optionally be configured such that delivering the therapy includes delivering spinal cord stimulation (SCS) to a lumbar or cervical region of the spinal cord.

In Example 35, the subject matter of Example 34 may optionally be configured such that delivering the therapy includes delivering SCS to at least two of a lumbar region, a thoracic region or a cervical region of the spinal cord.

In Example 36, the subject matter of any one or any combination of Examples 21-35 may optionally be configured such that the first parameter set and the second parameter set include a different parameter value or a different range of parameter values for at least one parameter selected from the group of parameter consisting of: frequency, pulse width, burst duration for a burst of pulses, active electrodes, fractionalization values for active electrodes.

In Example 37, the subject matter of any one or any combination of Examples 21-36 may optionally be configured such that the blood pressure demand event includes a posture change or an activity change for the patient.

In Example 38, the subject matter of any one or any combination of Examples 21-37 may optionally be configured such that the blood pressure demand event includes at least one of acute decompensation in heart failure, arrhythmia, or bradycardia.

In Example 39, the subject matter of any one or any combination of Examples 21-38 may optionally be configured such that the blood pressure demand event includes at least one of neurally-mediated hypotension, decreases in blood volume, anaphylactic shock or medication intake.

In Example 40, the subject matter of any one or any combination of Examples 21-39 may optionally be configured such that determining the actual or anticipated blood pressure demand event includes sensing blood pressure to determine the blood pressure event.

In Example 41, the subject matter of any one or any combination of Examples 21-40 may optionally be configured such that determining the actual or anticipated blood pressure demand event includes sensing evoked compound action potentials associated with a blood pressure response.

In Example 42, the subject matter of any one or any combination of Examples 21-41 may optionally be configured such that determining the actual or anticipated blood pressure demand event includes sensing activity.

In Example 43, the subject matter of any one or any combination of Examples 21-42 may optionally be configured such that determining the actual or anticipated blood pressure demand event includes sensing posture.

In Example 44, the subject matter of any one or any combination of Examples 21-43 may optionally be configured such that determining the actual or anticipated blood pressure demand event includes receiving via a user interface a user inputted signal.

In Example 45, the subject matter of any one or any combination of Examples 21-44 may optionally be configured to optimize the first and second parameter sets to provide the desired blood pressure responses.

In Example 46, the subject matter of Example 45 may optionally be configured such that optimizing the first and second parameter sets includes detecting blood pressure or another indicator of sympathetic tone, and using the detected blood pressure or other indicator of sympathetic tone to optimize the first and second parameter sets.

In Example 47, the subject matter of Example 45 may optionally be configured such that optimizing the first and second parameter sets includes detecting paresthesia coverage in lower legs when the neuromodulation energy is delivered using the first parameter set.

In Example 48, the subject matter of Example 45 may optionally be configured such that optimizing the first and second parameter sets includes optimizing at least one of the first and second parameter sets for pain relief.

In Example 49, the subject matter of Example 45 may optionally be configured such that optimizing the first and second parameter sets includes optimizing neuromodulation frequencies to provide the desired blood pressure responses.

In Example 50, the subject matter of Example 45 may optionally be configured such that optimizing the first and second parameter sets includes implementing an optimization schedule to determine when the first and second parameters sets are optimized.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
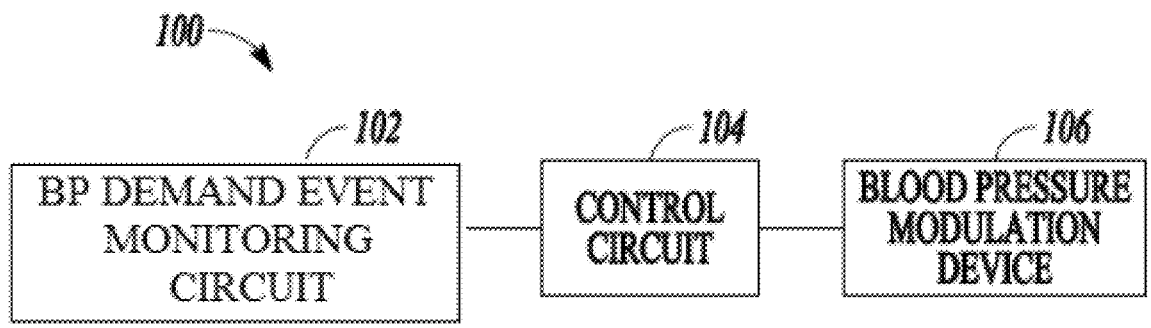
FIG. 1 illustrates an embodiment of a system for modulating blood pressure.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a device-based system and method for controlling blood pressure. Research has suggested that dynamic changes in blood pressure are associated with peroneal nerve activity. Electrical stimulation targeted at such pathways can reduce blood pressure specifically during dynamic swings associated with the exercise pressor reflex. Such electrical stimulation is likely to reduce sympathetic tone and subsequently dilate peripheral vessels in order to reduce blood pressure. An example of the system for controlling blood pressure includes a spinal cord stimulation (SCS) system. Other examples of the system for controlling blood pressure includes systems for delivering dorsal root ganglia stimulation, sympathetic chain modulation, and peripheral sympathetic nerve modulation.

SCS has been applied in treating pain and cardiovascular diseases including hypertension. Beneficial effects of SCS in a patient may vary over time based on physiological or lifestyle changes of the patient. Thus, parameters controlling the waveform of the neuromodulation energy delivered for the SCS should be dynamically adjusted or optimized to accommodate for these changes. Examples of such parameters include electrode configuration, pulse frequency (or inter-pulse interval), pulse width, and pulse amplitude. The waveform may include a simple pattern of pulses with an unchanging pulse width, amplitude, and pulse frequency, or may include more complex patterns of pulses that vary one or more of the pulse width, amplitude and pulse frequency within a pattern. The waveform may include discrete pulses of various shapes, or may include a more continuous waveform shape. Thus, there is a need for a system that delivers SCS to control a patient's blood pressure (e.g. treat a patient's hypertension) and automatically respond to an actual or anticipated blood pressure demand event, which is indicated for a blood pressure change, by delivering neuromodulation energy. For example, a desirable treatment option for a patient who has elevated exercise pressor reflex may be to react to dynamic swings in the patient's blood pressure and enable the therapy when it is needed by the patient, or for a patient who is supine hypertensive and experiences orthostatic intolerance may be to enable the therapy only when it is needed by the patient to improve the patient's blood pressure response to postural transitions. In another example, the system may provide for battery management to extend battery life by delivering therapy only when it is needed, when the therapy is delivered by a battery-powered device, such as an implantable device.

The present system can include a therapy device to deliver one or more therapies for modulating blood pressure, and may be configured to determine an actual or anticipated blood pressure demand event indicated for a blood pressure change. In one embodiment, the therapy device may include a chronically implanted neuromodulation device to deliver SCS. One or more signals may be processed to extract information used to maintain blood pressure within a prescribed range. In various embodiments, the system may detect onset of the exercise pressor reflex and treats its effects by delivering SCS to substantially reduce damaging effects of high blood pressure on the cardiovascular system. In various embodiments, the system may modulate or optimize stimulation parameters and provide as-needed SCS therapy based on the activity of the patient. In various embodiments, the system may execute an algorithm that automatically determines an optimal therapy for a given physiological parameter. The optimization of the therapy may include adjusting stimulation parameters such as electrode configuration, relatively continuous waveform shape, pulse pattern, pulse waveform shape, pulse frequency, duty cycle, pulse width, and pulse amplitude, and may also include adjusting stimulation paradigms such as kilohertz frequency stimulation and burst stimulation.

FIG. 1 illustrates an embodiment of a system 100 for modulating blood pressure of a patient. System 100 may include a blood pressure demand event monitoring circuit 102, a blood pressure modulating device 106, and a control circuit 104. The blood pressure demand event monitoring circuit 102 may receive a signal from a user interface indicating that a user has determined that there is an actual or anticipated blood pressure demand event. The blood pressure demand event monitoring circuit 102 may sense signals from the patient and generate one or more physiological parameters and optionally one or more functional parameters using the sensed signals. The one or more physiological parameters may include one or more blood pressure parameters indicative of one or more of the blood pressure or a vascular resistance of the patient, and/or may include one or more activity parameters indicative of one or more of an activity level or a postural change of the patient. The one or more functional parameters may include one or more activity parameters indicative of one or more of the activity level or the postural change of the patient. Thus, in various embodiments, blood pressure demand event monitoring circuit 102 may generate one or more blood pressure parameters and one or more activity parameters. The one or more blood pressure parameters are one or more physiological parameters, while the one or more activity signal can include one or more physiological parameters and/or one or more functional parameters. The blood pressure demand event monitoring device 106 may deliver a therapy modulating the blood pressure. Examples of such a therapy include an SCS, dorsal root ganglia stimulation, sympathetic chain modulation, and peripheral sympathetic nerve modulation. Control circuit 104 can control the therapy using therapy parameters, receive the one or more blood pressure parameters and the one or more activity parameters, analyze changes in the one or more blood pressure parameters correlated to changes in the one or more activity parameters, and adjust the therapy parameters using an outcome of the analysis.

In various embodiments, circuits of system 100, including various embodiments of its components discussed in this document, may be implemented using a combination of hardware and software. For example, the blood pressure demand event monitoring circuit 102, including its various embodiments discussed in this document, and control circuit 104 may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
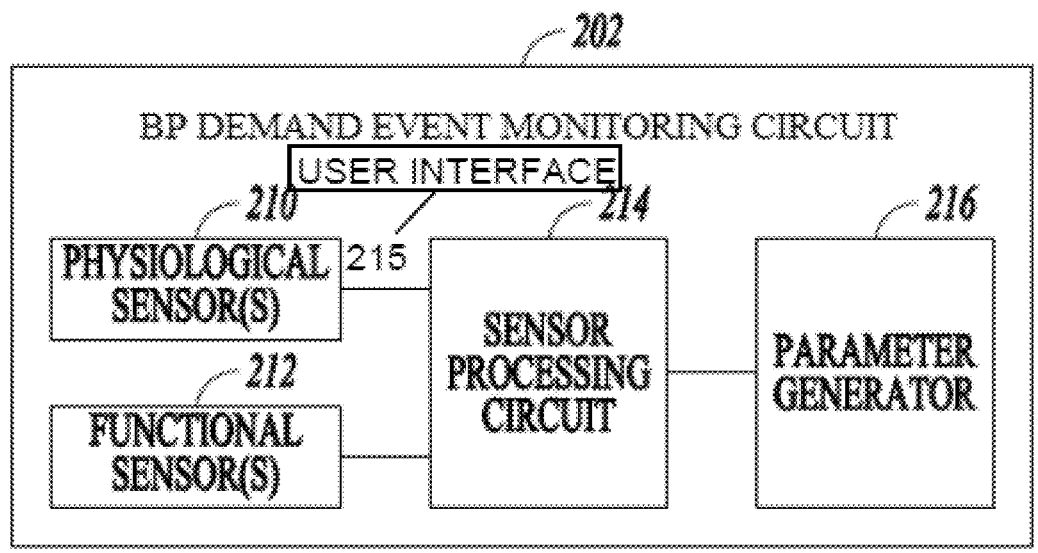
FIG. 2 illustrates an embodiment of a blood pressure monitoring circuit, such as may be used in the system of FIG. 1.

FIG. 2 illustrates an embodiment of a blood pressure demand event monitoring circuit 202, which represent an example of blood pressure monitoring circuit 102. The blood pressure demand event monitoring circuit 202 may include one or more physiological sensors 210, one or more functional sensors 212 (if needed), a sensor processing circuit 214, and a parameter generator 216. The blood pressure demand event monitoring circuit 202 may include a user interface 215 to receive user indications that the blood pressure event is occurring or anticipated.

The physiological sensor(s) 210 may sense one or more physiological signals each indicative of a physiological function or state of the patient. In various embodiments, the physiological sensor(s) 210 may include an invasive sensor (e.g., implantable sensor) or a non-invasive sensor (a wearable sensor). In various embodiments, one or more physiological signals include one or more signals indicative one or more of a blood pressure or a vascular resistance of the patient. In various embodiments, one or more physiological signals may also include one or more signals indicative one or more of an activity level or a posture change of the patient. The physiological sensor may be configured for use to detect an autonomic balance indicator (ABI), which may function as indicator of sympathetic tone.

A proposed mechanism of SCS is an inhibition of sympathetic activity. Various embodiments assess ABI using one or various combinations of parameters, such as heart rate variability (HRV), heart rate turbulence (HRT), electrogram features, activity, respiration, and pulmonary artery pressure. These parameters are briefly discussed below. Various embodiments provide closed loop control of the treatment using ABI.

HRV is one technique that has been proposed to assess autonomic balance. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and vagus nerve activity.

The time interval between intrinsic ventricular heart contractions changes in response to the body's metabolic need for a change in heart rate and the amount of blood pumped through the circulatory system. For example, during a period of exercise or other activity, a person's intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform techniques, so that its spectral frequency components can be analyzed and divided into low and high frequency bands. The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as autoregression) technique from the time domain into the frequency domain. Such calculations require significant amounts of data storage and processing capabilities. Additionally, such transformation calculations increase power consumption, and shorten the time during which the implanted battery-powered device can be used before its replacement is required.

One example of an HRV parameter is SDANN (standard deviation of averaged NN intervals), which represents the standard deviation of the means of all the successive 5 minutes segments contained in a whole recording. Other HRV parameters can be used.

HRT is the physiological response of the sinus node to a premature ventricular contraction (PVC), consisting of a short initial heart rate acceleration followed by a heart rate deceleration. HRT has been shown to be an index of autonomic function, closely correlated to HRV. HRT is believed to be an autonomic baroreflex. The PVC causes a brief disturbance of the arterial blood pressure (low amplitude of the premature beat, high amplitude of the ensuing normal beat). This fleeting change is registered immediately with an instantaneous response in the form of HRT if the autonomic system is healthy, but is either weakened or missing if the autonomic system is impaired.

By way of example and not limitation, it has been proposed to quantify HRT using Turbulence Onset (TO) and Turbulence Slope (TS). TO refers to the difference between the heart rate immediately before and after a PVC, and can be expressed as a percentage. For example, if two beats are evaluated before and after the PVC, TO can be expressed as:

$$TO\% = \frac{(RR_{+1} + RR_{+2}) - (RR_{-2} + RR_{-1})}{(RR_{-2} + RR_{-1})} * 100.$$

RR-2 and RR-1 are the first two normal intervals preceding the PVC and RR+1 and RR+2 are the first two normal intervals following the PVC. In various embodiments, TO is determined for each individual PVC, and then the average value of all individual measurements is determined. However, TO does not have to be averaged over many measurements, but can be based on one PVC event. Positive TO values indicate deceleration of the sinus rhythm, and negative values indicate acceleration of the sinus rhythm. The number of R-R intervals analyzed before and after the PVC can be adjusted according to a desired application. TS, for example, can be calculated as the steepest slope of linear regression for each sequence of five R-R intervals. In various embodiments, the TS calculations are based on the averaged tachogram and expressed in milliseconds per RR interval. However, TS can be determined without averaging. The number of R-R intervals in a sequence used to determine a linear regression in the TS calculation also can be adjusted according to a desired application.

Rules or criteria can be provided for use to select PVCs and for use in selecting valid RR intervals before and after the PVCs. A PVC event can be defined by an R-R interval in some interval range that is shorter than a previous interval by some time or percentage, or it can be defined by an R-R interval without an intervening P-wave (atrial event) if the atrial events are measured. Various embodiments select PVCs only if the contraction occurs at a certain range from the preceding contraction and if the contraction occurs within a certain range from a subsequent contraction. For example, various embodiments limit the HRT calculations to PVCs with a minimum prematurity of 20% and a post-extrasystole interval which is at least 20% longer than the normal interval. Additionally, pre-PVC R-R and post-PVC R-R intervals are considered to be valid if they satisfy the condition that none the of the beats are PVCs. One HRT process, for example, excludes RR intervals that are less than a first time duration, that are longer than a second time duration, that differ from a preceding interval by more than a third time duration, or that differ from a reference interval by a predetermined amount time duration or percentage. In an embodiment of such an HRT process with specific values, RR intervals are excluded if they are less than 300 ms, are more than 2000 ms, differ from a preceding interval by more than 200 ms, or differ by more than 20% from the mean of the last five sinus intervals. Various embodiments of the present subject matter provide programmable parameters, such as any of the parameters identified above, for use in selecting PVCs and for use in selecting valid RR intervals before and after the PVCs.

Various device embodiments may include means for pacing a ventricle, such as at least one ventricular pacing lead. To measure autonomic balance for closed-loop therapy titration, the device intermittently introduces or senses a PVC, and measures the resulting HRT, as described above.

Benefits of using HRT to monitor autonomic balance include the ability to measure autonomic balance at a single moment in time. Additionally, unlike the measurement of HRV, HRT assessment can be performed in patients with frequent atrial pacing. Further, HRT analysis provides for a simple, non-processor-intensive measurement of autonomic balance. Thus, data processing, data storage, and data flow are relatively small, resulting in a device with less cost and less power consumption. Also, HRT assessment is faster than HRV, requiring much less R-R data. HRT allows assessment over short recording periods similar in duration to typical neural stimulation burst durations, such as on the order of tens of seconds, for example.

Various embodiments extract various ECG features to provide an ABI. Examples of such features include heart rate, which can be used to form HRV, and heart rate turbulence. Other features can be extracted from the ECG, and one or various combinations of these features can be used to provide an ABI. Various embodiments provide blood pressure to provide an ABI. For example, some embodiment sense pulmonary artery blood pressure.

Activity sensors can be used to assess the activity of the patient. Sympathetic activity naturally increases in an active patient, and decreases in an inactive patient. Thus, activity sensors can provide a contextual measurement for use in determining the autonomic balance of the patient. Various embodiments, for example, provide a combination of sensors to trend heart rate and/or respiration rate to provide an indicator of activity.

Two methods for detecting respiration involve measuring a transthoracic impedance and minute ventilation. Respiration can be an indicator of activity, and can provide an explanation of increased sympathetic tone. For example, it may not be appropriate to change or modify a treatment for modulating autonomic tone due to a detected increase in sympathetic activity attributable to exercise.

Respiration measurements (e.g. transthoracic impedance) can also be used to measure Respiratory Sinus Arrhythmia (RSA). RSA is the natural cycle of arrhythmia that occurs through the influence of breathing on the flow of sympathetic and vagus impulses to the sinoatrial node. The rhythm of the heart is primarily under the control of the vagus nerve, which inhibits heart rate and the force of contraction. The vagus nerve activity is impeded and heart rate begins to increase when a breath is inhaled. When exhaled, vagus nerve activity increases and the heart rate begins to decrease. The degree of fluctuation in heart rate is also controlled significantly by regular impulses from the baroreceptors (pressure sensors) in the aorta and carotid arteries. Thus, a measurement of autonomic balance can be provided by correlating heart rate to the respiration cycle.

Muscle sympathetic nerve activity (MSNA) may be used to monitor sympathetic activity.

In various embodiments, physiological sensor(s) 210 can include one or more sensors selected from the following examples (1)-(7):
  (1) A blood pressure sensor to sense a blood pressure or a surrogate of the blood pressure of the patient and produce a blood pressure signal indicative of the blood pressure. The blood pressure sensor may be an intravascular sensor to sense the blood pressure directly or an extravascular sensor to sense the surrogate of the blood pressure. Examples of the blood pressure sensor may include:
    a. an invasive arterial pressure sensor to be placed in an artery to sense an arterial blood pressure being a direct measure of an arterial blood pressure;
    b. a non-invasive blood pressure cuff to sense an external blood pressure;
    c. a heart sound sensor to sense a heart sound signal indicative of at least second heart sounds (S2), such as an accelerometer or a microphone, in an implantable device or incorporated into the distal end of a lead connected to the implantable device;
    d. a photoplethysmography (PPG) sensor to sense a PPG signal;
    e. an impedance sensor to sense an impedance signal indicative of the blood pressure or the vascular resistance, such as an electrical bioimpedance sensor to sense an electrical bioimpedance signal or an impedance cardiography sensor to sense an impedance cardiographic signal (noninvasive measurement of electrical impedance of the thorax);
    f. a neural sensor to sense a nerve signal indicative of sympathetic tone (which in turn indicates blood pressure), such as electrode(s) incorporated into the distal end of a lead connected to the implantable device to sense local field potentials and/or evoked compound action potentials; and g. a sensor to sense an electroencephalographic (EEG) signal e of activity or the sympathetic tone.

(2) Cardiac sensing electrodes to sense a cardiac signal allowing for detection of heart rate and heart rate variability (HRV).

(3) A respiratory sensor to sense a respiratory signal indicative of respiratory rate.

(4) A galvanic skin response (GSR) sensor to sense a GSR signal indicative of sweating.

(5) Electromyogram (EMG) sensing electrodes to sense an EMG signal indicative of muscle activation.

(6) A peripheral vascular sensor to sensor one or more of peripheral perfusion or vascular resistance, such as a flow sensor, a perfusion sensor; and a temperature sensor.

(7) A chemical sensor to sense one or more chemical biomarkers of exertion, such as one or more of lactate or interleukin 6 (IL-6).

Functional sensor(s) 212, when needed, may sense one or more functional signals each indicative of a physical activity or state of the patient. In various embodiments, functional sensor(s) 212 may include an invasive sensor (e.g., implantable sensor) or a non-invasive sensor (e.g., wearable sensor). In various embodiments, the one or more functional signals are indicative of one or more of an activity level or a postural change of the patient. In various embodiments, functional sensor(s) 212 may include an activity sensor to sense one or more of activity or postural change of the patient, and can produce an activity signal indicative of one or more of an activity level or a postural change. Examples of such an activity sensor include one or more of an accelerometer or a gyroscope. The accelerometer may sense the activity and/or the postural change of the patient, and may produce an accelerometer signal indicative of the activity level and/or postural change. The gyroscope can sense angular acceleration indicative of angular postural change (in roll, pitch, and yaw) of the patient, and can produce a gyroscope signal indicative of the angular postural change.

The sensor processing circuit 214 may process the one or more physiological signals produced by physiological sensor(s) 210 and the one or more functional signals produced by functional sensor(s) 212. In various embodiments, the processing may include signal conditioning and detection of signal features (e.g., heart sounds and cardiac depolarizations allowing for measurement of parameters).

The parameter generator 216 may generate one or more physiological parameters indicative of the physiological function or state of the patient using the processed one or more physiological signals, and may generate one or more functional parameters each indicative of the physical activity or state of the patient using the processed one or more functional signals. In various embodiments, the one or more physiological parameters can include one or more blood pressure parameters indicative of one or more of a blood pressure or a vascular resistance of the patient, and may activity parameters indicative of one or more of an activity level or a postural change of the patient. The one or more functional parameters may include one or more activity parameters indicative of one or more of an activity level or a postural change of the patient. In one embodiment, the parameter generator 216 may generate a blood pressure parameter and at least one physiological parameter being an activity parameter.

These parameters allow for analysis of correlation between the activity level and/or the postural change and changes in the blood pressure and/or vascular resistance. In various embodiments, the one or more physiological parameters can include one or more blood pressure parameters each indicative of one or more of the blood pressure or the vascular resistance. The one or more blood pressure parameters may each be a direct measure of a blood pressure or a surrogate for the blood pressure, and can include one or more parameters selected from the following examples (1)-(6):

(1) An arterial pressure measured from the arterial blood pressure signal.

(2) A blood pressure measured from the external blood pressure signal.

(3) A heart sound parameter measured from the heart sound signal, such as a parameter measured from S2 in the heart sound signal. S2 can be used as an indirect measure of the blood pressure).

(4) A PPG parameter measured from the PPG signal, such as pulse transit time, pulse amplitude, pulse volume, systolic pressure, and/or diastolic pressure.

(5) A hemodynamic parameter indicative of blood pressure or vascular resistance measured from the electrical bioimpedance signal or the impedance cardiographic signal.

(6) A parameter being a measure of the sympathetic tone measuring from the nerve signal or the EEG signal.

The one or more physiological parameters may also include one or more activity parameters each indicative of one or more of the activity level or the postural change. Such one or more activity parameters (each being a physiological parameter) can include one or more parameters selected from the following examples (1)-(6):

(1) A heart rate and/or an HRV parameter measured from the cardiac signal. Time and frequency domain measures of the heart rate and HRV can be used to detect exertion. HRV is the beat-to-beat variance in cardiac cycle length over a period of time. An "HRV parameter" as used in this document includes any parameter being a measure of the HRV, including any qualitative expression of the beat-to-beat variance in cardiac cycle length over a period of time. Examples of the HRV parameters include standard deviation of normal-to-normal intervals (SDNN), standard deviation of averages of normal-to-normal intervals (SDANN), ratio of low-frequency (LF) HRV to high-frequency (HF) HRV (LF/HF ratio), HRV footprint, root-mean-square of successive differences (RMSSD), and percentage of differences between normal-to-normal intervals that are greater than 50 milliseconds (pNN50). The HRV can also include a measure for respiratory sinus arrhythmia (RSA), which is essentially a short-term HRV measure.

(2) A respiration rate measured from the respiratory signal. The respiratory rate increases with increased sympathetic activation or increased exertion. Respiration can also be used to analyze autonomic tone through respiration sinus arrhythmia.

(3) A GSR parameter indicative of sweating, measured from the GSR signal. Sweating due to increased activity can lead to reduced resistance and increased skin conductivity. GSR also provides a measure of autonomic tone with increased sympathetic activity causing in increase in skin conductance. Time domain measures for mean skin conductance and the number of skin conductance fluctuations can be measured are examples of GSR measures.

(4) A muscular activity parameter measured from the EMG. Pattern analysis, time domain (amplitude, latency, etc.) measures, and frequency domain measures can be used to detect muscle activation. Muscle activation during exercise increases sympathetic tone and blood pressure via the exercise pressor response.

(5) A peripheral vascular parameter measured from the peripheral vascular signal and indicative of perfusion and vascular resistance in peripheral blood vessels.

(6) An exertion parameter measured using the chemical biomarkers and indicative of changes in exertion.

In various embodiments, the one or more functional parameters may include one or more activity parameters each indicate one or more of the activity level or the postural change. Such one or more activity parameters (each being a functional parameter) can include one or more parameters selected from the following examples (1) and (2):

(1) an activity parameter indicative of the activity level of the patient, measured using the accelerometer signal, to correlate changes in the physiological parameter indicative of the blood pressure or the vascular resistance of the patient to changes in the patient's activity level; and (2) a postural parameter indicative of the postural change of the patient, measured using the gyroscope signal and/or the accelerometer signal, to correlate changes in the physiological parameter indicative of the blood pressure or the vascular resistance of the patient to changes in the postural change of the patient.

Figure 3:
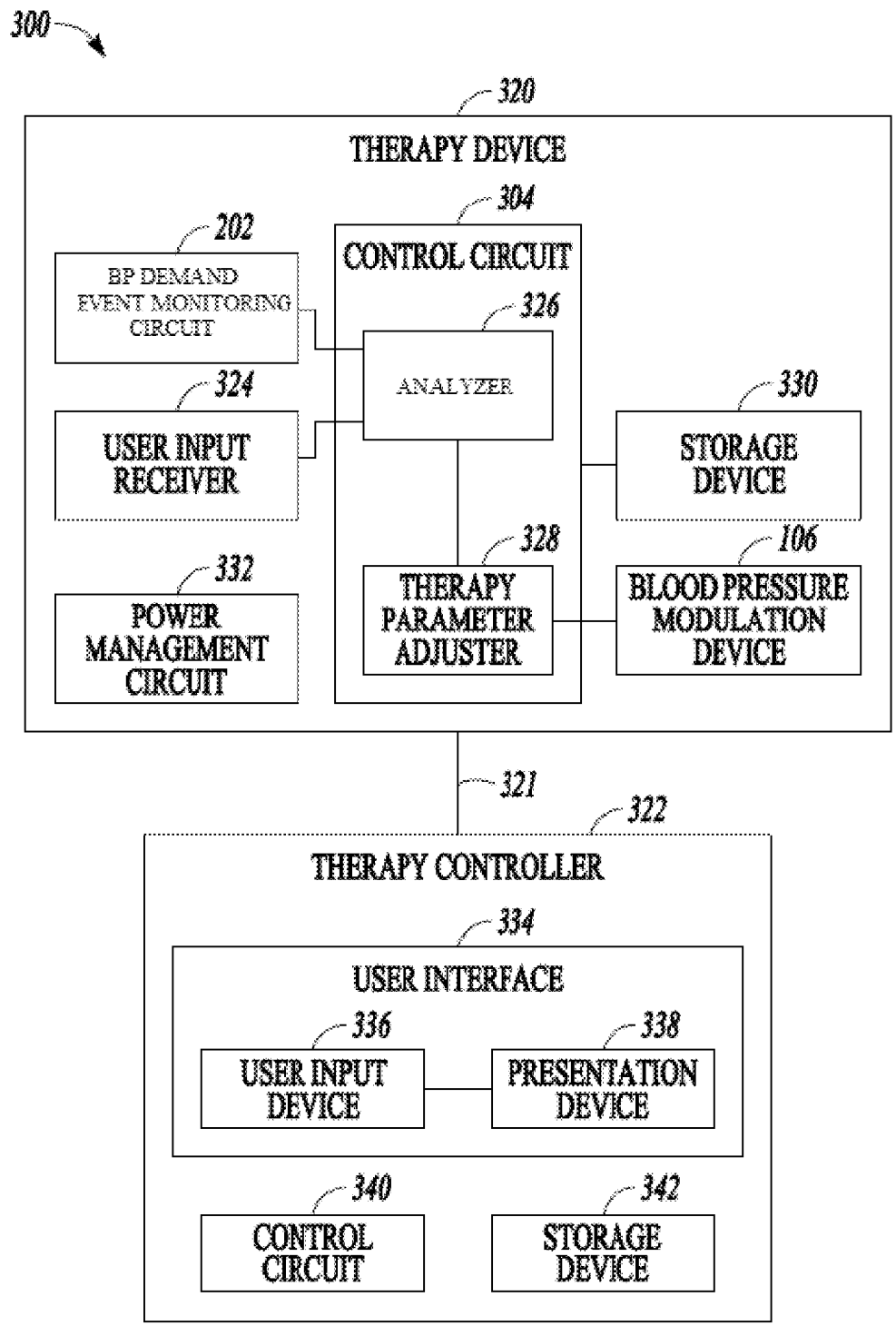
FIG. 3 illustrates another embodiment of a system for modulating blood pressure.

FIG. 3 illustrates an embodiment of a system 300 for modulating blood pressure. The system 300 represents a more specific example of the system 100 illustrated in FIG. 1 and includes a therapy device 320 and a therapy controller 322. In various embodiments, the therapy device 320 and therapy controller 322 may be integrated into a single device or implemented as two or more separate devices. In various embodiments, the therapy device 320 may include multiple devices coupled to each other via wired and/or wireless links. The therapy device 320 and therapy controller 322 may be integrated into a single device with a user interface, such as for delivering therapy percutaneously or transcutaneously. In embodiments using an implantable device, such as discussed below with reference to FIG. 4, the therapy device 320 may be implemented as the implantable device, and therapy controller 322 can be implemented as an external device. In various embodiments, the therapy device 320 may include an implantable device or a front-end device for sensing and therapy delivery, while the therapy controller 322 may function as a user controller (for use by a physician or other caregiver or the patient) that include a user interface. In various embodiments, the therapy device 320 may includes an implantable device for the therapy delivery and implantable and/or noninvasive sensors communicatively coupled to that implantable device via wired and/or wireless links.

The therapy device 320 may include blood pressure demand event monitoring circuit 202, a user input receiver 324, a control circuit 304, blood pressure modulation device 106, a storage device 330, and a power management circuit 332. The user input receiver 324 may receive one or more user commands transmitted from therapy controller 322 via a wireless or wired link 321. In various embodiments, the one or more user commands can include any one or more of the following examples (1)-(3):

(1) A user command for activating or inhibiting the therapy.

(2) A user command indicating a beginning or end of a physical exercise.

(3) A user command indicating a beginning or end of rest (or sleep).

(4) User commands representing feedback from the patient. For example, the feedback can include indication for initiating a calibration of an optimization algorithm executed by control circuit 304.

The control circuit 304 can control delivery of the therapy modulating the blood pressure from blood pressure modulation device 106 using therapy parameters. In one embodiment, control circuit 304 controls delivery of SCS from a neuromodulation device using stimulation parameters.

The control circuit 304 may include a blood pressure analyzer 326 and a therapy parameter adjuster 328. The Blood pressure analyzer 326 can receive and analyze the one or more physiological parameters each indicative of the physiological function or state of the patient and optionally one or more functional parameters each indicative of the physical activity or state of the patient, and analyze the received parameters. Therapy parameter adjuster 304 can adjust the therapy parameters an outcome of the analysis. In various embodiments, the analysis can be based on the one or more blood pressure parameters and the one or more activity parameters. The one or more blood pressure parameters include one or more of the one or more physiological parameters received by blood pressure analyzer 326. The one or more activity parameters include one or more of the one or more physiological parameters received by blood pressure analyzer 326 and or the one or more functional parameters received by blood pressure analyzer 326. In some embodiments, blood pressure analyzer 326 can further receive the one or more user commands and include the received one or more user commands in the analysis of the one or more blood pressure parameters and the one or more activity parameters. In various embodiments, control circuit 304 can control delivery of the therapy from blood pressure modulation device 106 using the one or more blood parameters, the one or more activity parameters, and optionally the one or more user commands.

In various embodiments, therapy parameter adjuster 328 can approximately optimize the therapy parameters by executing an optimization algorithm. The optimization algorithm allows the therapy parameters to be set for an approximately optimal therapeutic effect as indicated by the one or more blood pressure parameters and the one or more activity parameters. In some embodiments, the one or more user commands (e.g., user commands representing feedback from the patient) can also be used by the optimization algorithm. In the embodiment in which the therapy includes SCS, the therapy parameters (i.e., stimulation parameters) can include, but are not limited to, electrode configuration, pulse waveform shape, pulse frequency, duty cycle, pulse width, and pulse amplitude, as well as parameters controlling a stimulation paradigm (e.g., kilohertz frequency stimulation, burst stimulation). In various embodiments, therapy parameter adjuster 328 allow for calibration of the optimization algorithm, such as on a periodic or as-needed basis. In one embodiment, the calibration is manually performed by a user such as a physician or other authorized caregiver using therapy controller 322. In one embodiment, the calibration is automatically performed according to a specified schedule, as triggered by a specified event (such as the optimal therapeutic effect falling outside a specified threshold), or in response to a user command entered using therapy controller 322. Exemplary methods for calibration include receiver operating characteristic analysis and psychometric curves. Psychometric curves can be used to correlate parameters measured from signals sensed from the patient with a direct or indirect blood pressure measure as stimulation settings and/or paradigms are shifted. By correlating the blood pressure measure to one or more physiological parameters measured using sensors, the efficiency and accuracy of the therapy system can be improved for delivering therapy when needed, such as when the risk of blood pressure elevation is indicated.

Storage device 330 can store data acquired by therapy device 320. For example, when therapy device 320 is implemented as the implantable device, storage device can be used to store data acquired by the implantable device for transmitted to the external device when needed. Examples of records to be stored storage device 330 include: (i) portions of the one or more blood signals and the one or more activity parameters allowing for trending of the one or more blood pressure parameters as a function of the one or more activity signals (e.g., trending of the change if blood pressure and/or vascular resistance of the patient as a function of the activity level and/or postural change of the patient), (2) record of therapy parameter settings that have been used and basis for each of the settings (e.g., values of the one or more blood pressure parameters and the one or more activity parameters used to optimize each setting), and (3) record of the one or more user commands (e.g., when SCS is temporarily activated or terminated by the patient).

The power management circuit 322 may control a power mode of therapy device 320 or system 300. In various embodiments, the power management circuit 322 may place the therapy device 320 or system 300 in a low-power mode while the patient is sleeping, as indicated by the activity parameter and/or a user command. For example, the patient may be considered to be sleeping when the activity parameter indicates the patient has an activity level under a sleeping threshold specified to indicate sleeping, or when the user command indicates a patient-specified sleeping period. The power management circuit 322 can resume to a normal operation mode in therapy device 320 or system 300 in response to a specified wake-up event. Examples of such wake-up event include expiration of the patient-specified sleeping period, a change in the activity parameter indicating the patient is no longer sleeping, and a change in the one or more physiological parameters exceeding a therapy threshold specified to indicate a need for therapy.

The therapy controller 322 may allow the user to receive information from the therapy device 320 and control operation of the therapy device 320. The therapy controller 322 may include a user interface 334, a control circuit 340, and a storage device 342. The user interface 334 may include a user input device 336 and a presentation device 338. The user input device 336 may receive information from the patient or the physician or other caregiver, including the one or more user commands. The presentation device 338 may include a display screen and/or other audio and/or visual presentation devices to present information about the patient's blood pressure and/or the operation status and history of therapy device 320. In one embodiment, a touchscreen may be used as user input device 858 and presentation device 860. The control circuit 3340 may control operation of therapy controller 322. The storage device 342 may store information transmitted from therapy device 320 as well as information for programming therapy device 320. In various embodiments, the system 300 may include one or more storage devices, such as a storage device in the front-end therapy device (e.g., an implantable device), a storage device in a controller/user interface device (e.g., an external device communicatively coupled to the implantable device via a wireless link) and one or more network ("cloud") storage devices, to store data for review by the patient and the physicians and other caregivers as well as researchers.

Figure 4:
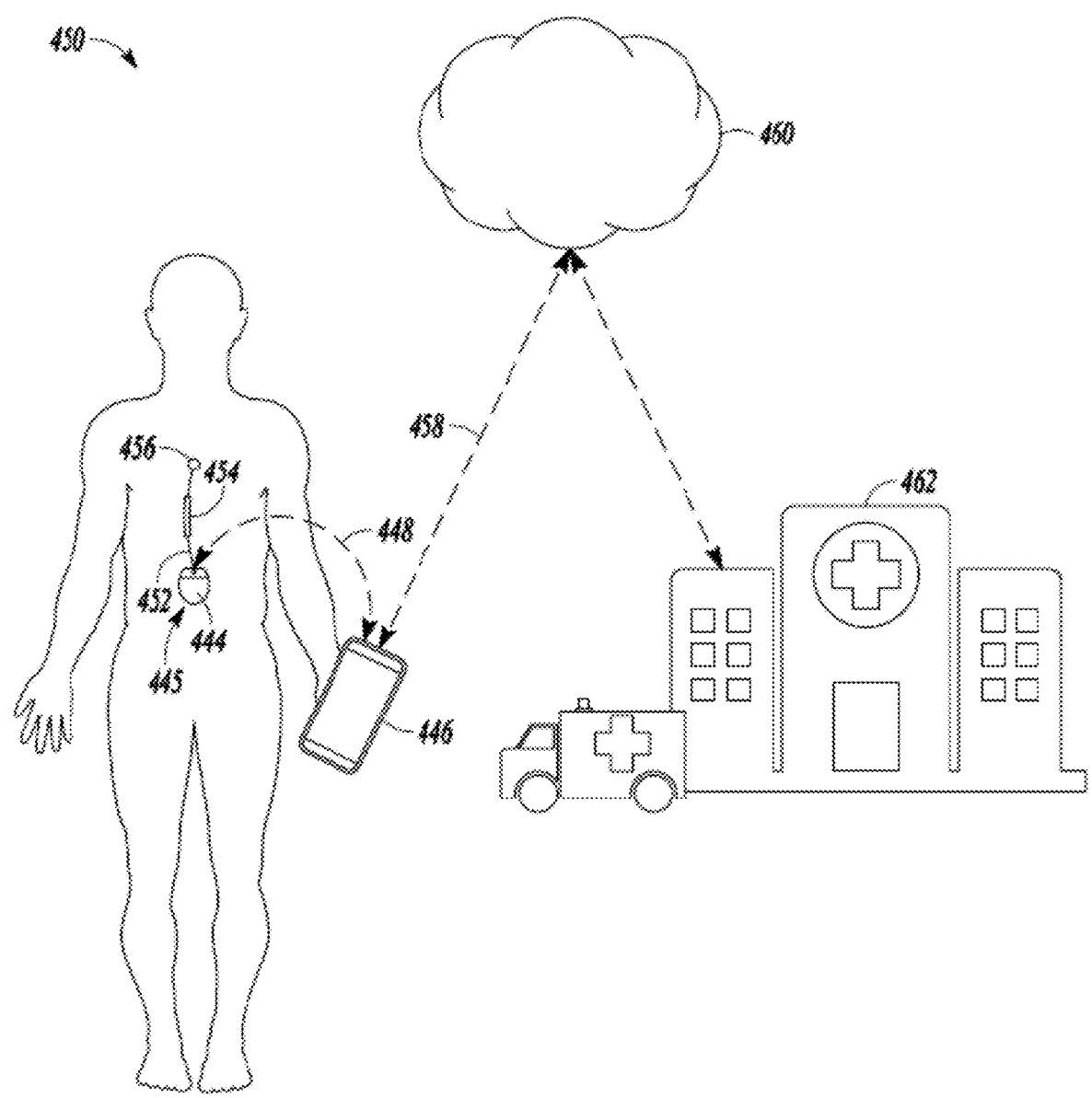
FIG. 4 illustrates an embodiment of an implantable system, such as one in which the system of FIG. 1 or FIG. 3 may be implemented, and portions of an environment in which the implantable system may be used.

FIG. 4 illustrates an embodiment of an implantable system 450 and portions of an environment in which system 450 may be used. The system 100 or 300 can be implemented in system 450. The system 450 may include an implantable system 445, a portable device 446 communicatively coupled to implantable system 445 via a wireless communication link 448, a network 460 communicatively coupled to portable device 446 via communication link 458, and medical facility 462 communicatively coupled to network 460. The implantable system 445 can include an implantable medical device 444, and an implantable lead or lead system 452 connected to the implantable medical device 444. A blood pressure demand event monitoring circuit such as blood pressure demand event monitoring circuit 102 (including its various embodiments) can be contained within the implantable medical device 444 or distributed in the implantable medical device 444 and the portable device 446. The implantable medical device 446 may include a therapy device such as blood pressure modulation device 106 to deliver a therapy that modulate blood pressure. In various embodiments, the portable device 446 may be implemented as a dedicated device or in a generic device such as a smartphone, a laptop computer, or a tablet computer. In various embodiments, therapy device 320 may be implemented in implantable system 445, and the therapy controller 322 can be implemented in portable device 446 or portable device 446 and network 460.

In the illustrated embodiment, the lead or lead system 452 may include an electrode or electrode array 454 and a sensor 456 shown by way of example, but not by way of restriction. In various embodiments, additional one or more electrodes may be incorporated onto implantable medical device 444. In the illustrated embodiment, the sensor 456 may represent an embodiment of a sensor (e.g., a heart sound sensor) that is incorporated into the lead or lead system 452 and to be positioned in or near the thoracic region. In another embodiment, the sensor may be embedded in the implantable medical device 444, which can be an implantable neuromodulator placed in the lumbar region (e.g., for delivering SCS). In various embodiments, one or more physiological sensors and the one or more functional sensors maybe incorporated into the lead or lead system 452, included in implantable medical device 444, or implemented as separate device, such as an implantable device or external (e.g., wearable) device, that may communicate with implantable medical device 444 wirelessly via telemetry.

In various embodiments, information related to the patient's blood pressure as well as other information about the patient and/or implantable system 445 can be produced by the implantable medical device 444 based on sensed signals and transmitted to the portable device 446 via communication link 448. The portable device 446 may selectively relay the received information to network 338 via communication link 458 to be stored, further analyzed, inform the patient's healthcare provider, and/or used to control delivery of the therapy from implantable medical device 444. When the information indicates that the patient needs medical attention, such as when the system 450 is unable to automatically adjust the therapy parameters to maintain the patient's blood pressure within a specified range, a notification may be transmitted to the medical facility 462 from the network 460.

In various embodiments, the portable device 446 and one or more devices within the network 460 and/or the medical facility 462 may allow a user such as a physician or other caregiver and/or the patient to communicate with the implantable medical device 444, for example to initialize and adjust settings of the implantable medical device 444. For example, portable device 446 may inform the patient the blood pressure and/or other information produced by implantable medical device 644, and allow the patient to turn implantable medical device 444 on and off and/or adjust certain patient-programmable parameters controlling delivery of the therapy.

The sizes and shapes of the elements of the system 450 and their locations relative to the patient's body are illustrated by way of example and not by way of restriction. The system 450 is discussed as a specific application of the system for modulating blood pressure according to various embodiments of the present subject matter. In various embodiments, the present subject matter may be applied in any type of blood pressure modulation in controlling therapy delivery.

Figure 6:
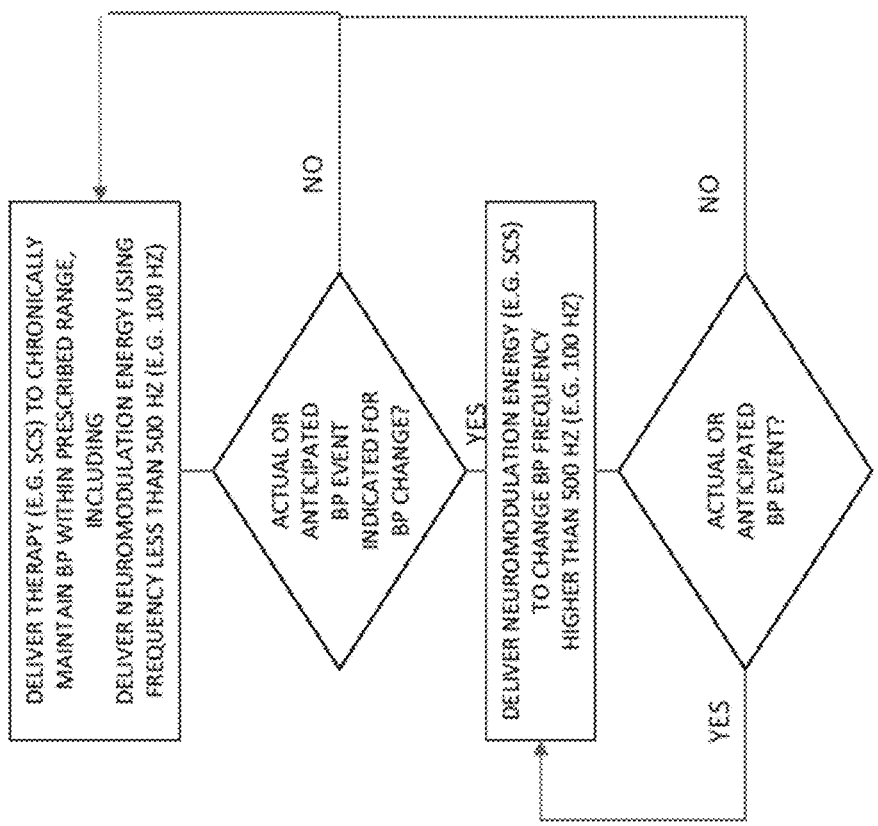
FIG. 6 illustrates a method that is a more specific embodiment of the method illustrated in FIG. 5.
Figure 5:
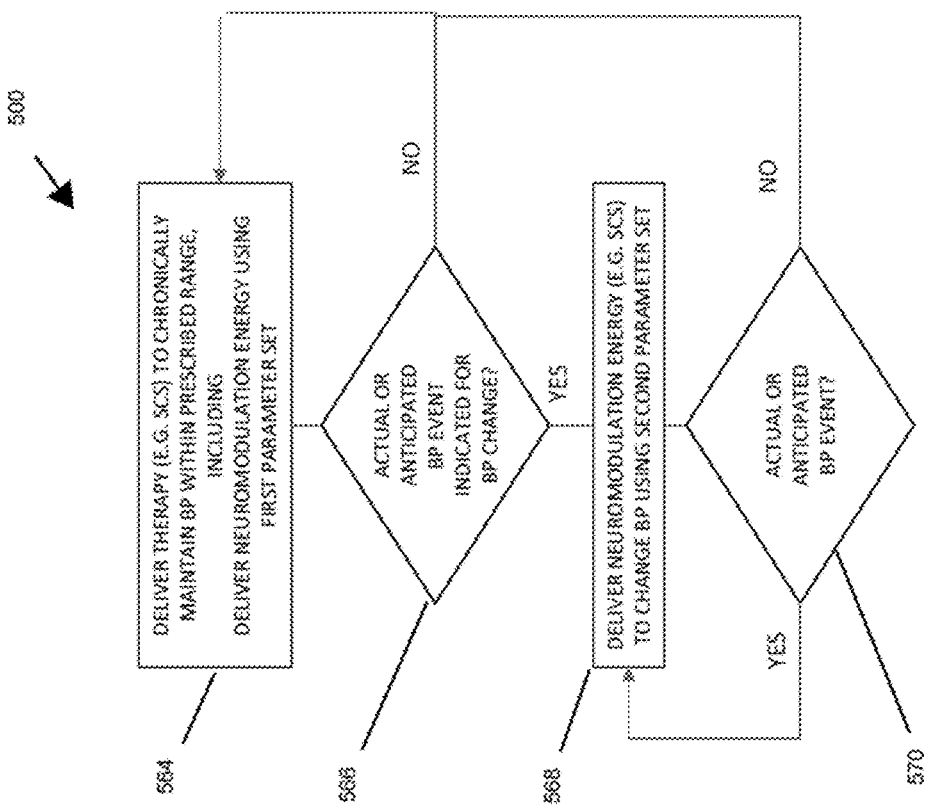
FIG. 5 illustrates an embodiment of a method 500 for controlling blood pressure of a patient.

FIG. 5 illustrates an embodiment of a method 500 for controlling blood pressure of a patient. The system 100 or 300 may be programmed to perform method 500. FIG. 6 illustrates a method 600 that is a more specific embodiment of the method 500 illustrated in FIG. 5.

At 564, therapy is delivered to the patient. By way of example, the therapy may be SCS delivered to the thoracic region (e.g. T10-T12) to provide paresthesia in the legs. In some embodiments, neuromodulation parameters (e.g. active electrodes, anodic and cathodic current contributions of the active electrodes, amplitude, pulse width, pulse shape, pulse patterns, continuation waveform shape) may be adjusted until the patient perceives paresthesia relatively uniformly throughout the legs. Other portions of the spinal cord, including the cervical and lumbar regions, and other portions of the thoracic region may be stimulated. The modulation parameters that achieves the desired paresthesia coverage or desired pain relief may be referred to as a first parameter set. This first parameter set may be used to chronically maintain blood pressure within a prescribed range.

At 566, it is determined whether an actual or anticipated blood event that is indicated for a blood pressure change has occurred. An example of such events may include posture changes (e.g. lying down to standing up), activity, acute decompensation, arrhythmia, bradycardia, decreases in blood volume, anaphylactic shock, neurally-mediated hypotension, or medication intake. This may be determined using appropriate sensors (e.g. sensors of blood pressure, activity, posture, cardiac activity, etc.) and/or may be determined by user input. If the blood pressure event had not occurred, the process keeps on delivering the therapy as illustrated at 564. If the process has occurred, the process continues to 568 to address the BP event.

At 568, the neuromodulation energy is delivered using a second parameter set to change BP. The second parameter set includes at least one different value for at least one parameter to cause the BP change. For example, the neuromodulation energy delivered using the first parameter set may have a lower frequency than the neuromodulation energy delivered using the second parameter set. As generally illustrated in FIG. 6, the frequency of the neuromodulation energy delivered using the first parameter set may be below 500 Hz, and the frequency of the neuromodulation energy delivered using the second parameter set may be above 500 Hz. In some embodiments, the frequency of the neuromodulation energy delivered using the first parameter set may be within a range between 20 Hz to 200 Hz, and the frequency of the neuromodulation energy delivered using the second parameter set may be within a range between 700 Hz to 1500 Hz. For example, the frequency of the neuromodulation energy delivered using the first parameter set may be 100 Hz, and the frequency of the neuromodulation energy delivered using the second parameter set may be 1,000 Hz. Thus, for example, the SCS delivered at 100 Hz may maintain blood pressure at a relatively low range (lower than would be observed without SCS). The SCS delivered at 1,000 Hz may increase blood pressure (e.g. higher than would be observed without SCS). Therefore, delivering SCS with the second set of parameters may enable an increase in blood pressure higher than would be achieved if the SCS therapy using the first set of parameters was simply interrupted and no SCS was delivered. Other parameters may be modified in addition to or alternative to the frequency. For example, the neuromodulation energy delivered using the first parameter set and the neuromodulation energy delivered using the second parameter set have different waveform with different pulse patterns or waveform shapes.

At 570, the process determined whether the actual or anticipated blood pressure event is still present. The SCS may continue to be delivered using the second parameter set, as illustrated at 568, as long as it is indicated to change the blood pressure. If the event is no longer present, the process may return to 564 to deliver therapy to chronically maintain BP within the prescribed range.

Figure 7:
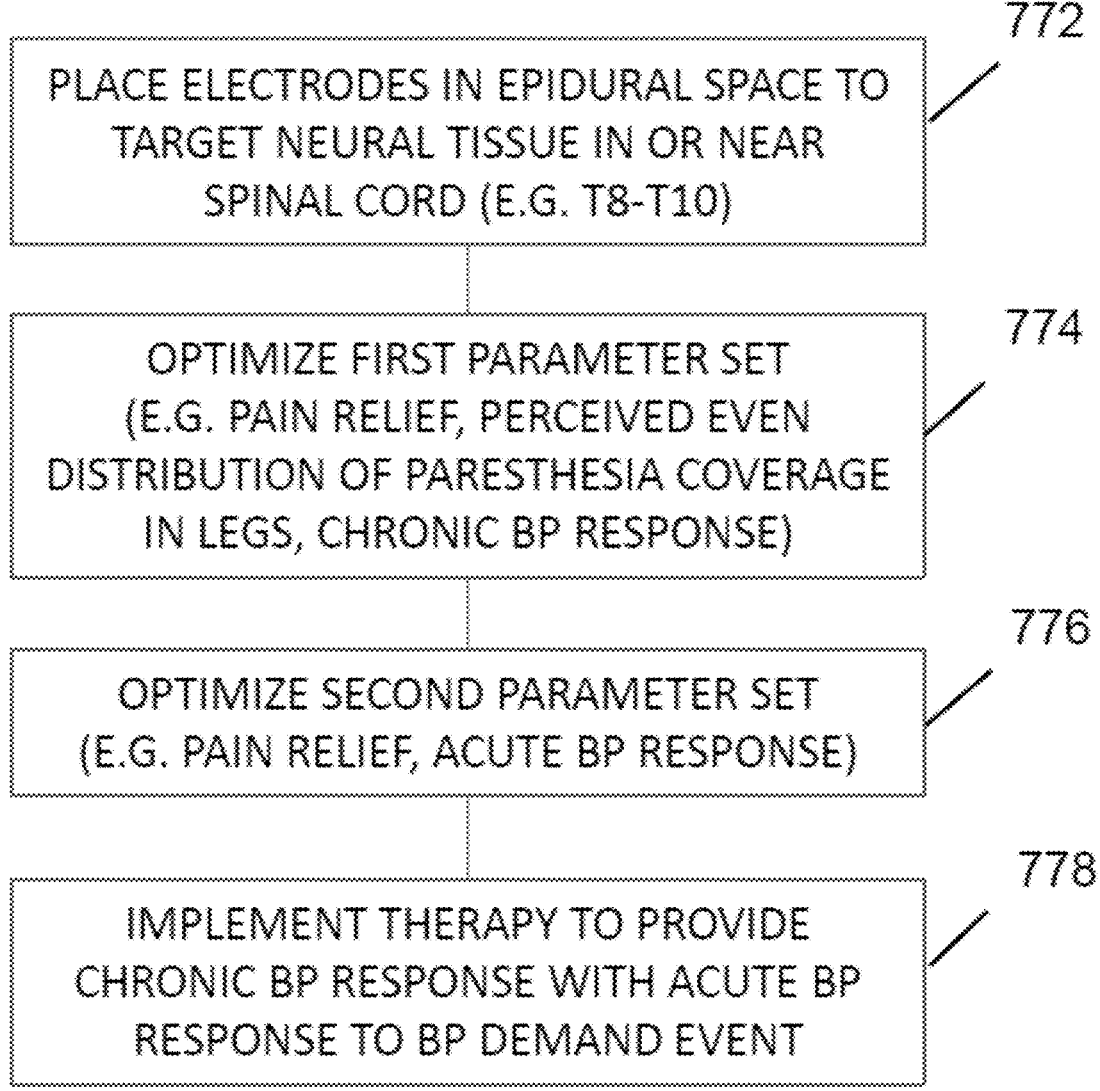
FIG. 7 illustrates an example of a procedure for setting up the system to provide blood pressure control.
Figure 8:
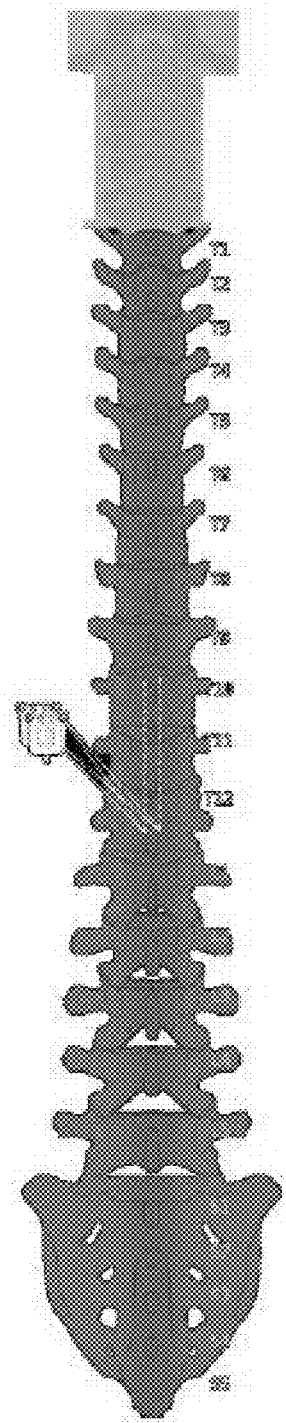
FIG. 8 illustrates an example of SCS lead placement to modulate the T10-T12 region.

FIG. 7 illustrates an example of a procedure for setting up the system to provide blood pressure control. At 772, electrodes are placed in the epidural space to target neural tissue in or near the spinal cord. The placements may be similar to conventional SCS to provide pain relieve for the legs (e.g. T10-T12). FIG. 8 illustrates an example of SCS lead placement to modulate the T10-T12 region. Some embodiments may target other regions using electrodes within the epidural space or using electrodes outside of the epidural space. By way of example, some regions that may be targeted may include the dorsal column the dorsal horn, the dorsal root ganglia, a dorsal root, a sympathetic chain or peripheral sympathetic nerve. Also, neuromodulation may be delivered to the lumbar region, the thoracic region or the cervical region. At 774, the first parameter set is optimized. For example, the embodiment that delivers SCS to the T10-T12 region may optimize the first parameter set by modifying parameters until the patient has adequate pain relief or perceives paresthesia in a desired location. For example, the optimization procedure may include attempting to provide paresthesia that is perceived as a generally uniform sensation through the legs or other region of the body. The neuromodulation energy applied using the first parameter set may be used to chronically maintain the blood pressure in a prescribed range (e.g. chronically lower blood pressure in a hypertensive patient). At 776, the second parameter set is optimized. The second parameter set is used to provide the blood pressure change in response to determining that an actual or anticipated blood pressure event, which is indicated for the blood pressure change, has or will occur. For example, the second parameter set may be selected to raise blood pressure to compensate for the blood pressure event. The optimization of these parameters may be based on pain relief or based on an acute blood pressure response or other autonomic balance indicator. At 778, the process continues to implement the therapy, such as illustrated in FIGS. 5-6, to provide the chronic blood pressure response with the acute blood pressure response for a blood pressure demand event.

Figure 9:
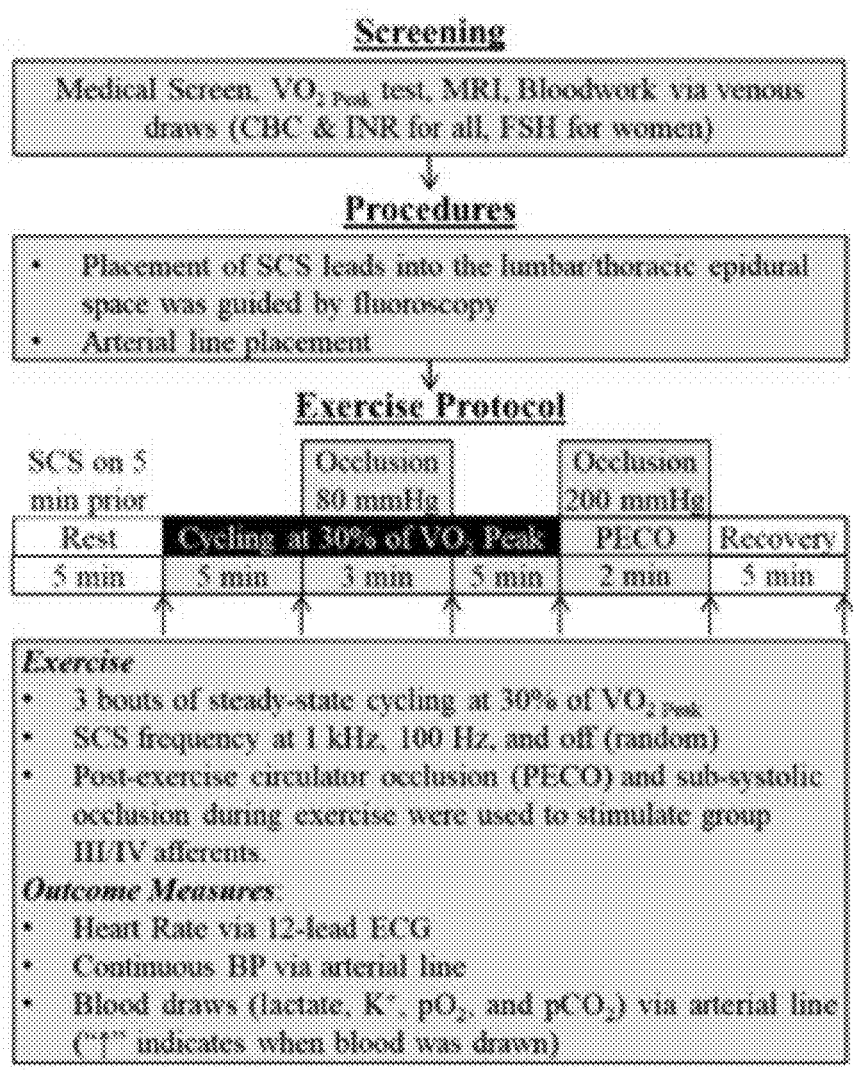
FIG. 9 illustrates screening, procedures and exercise protocol for an experiment.
Figure 10:
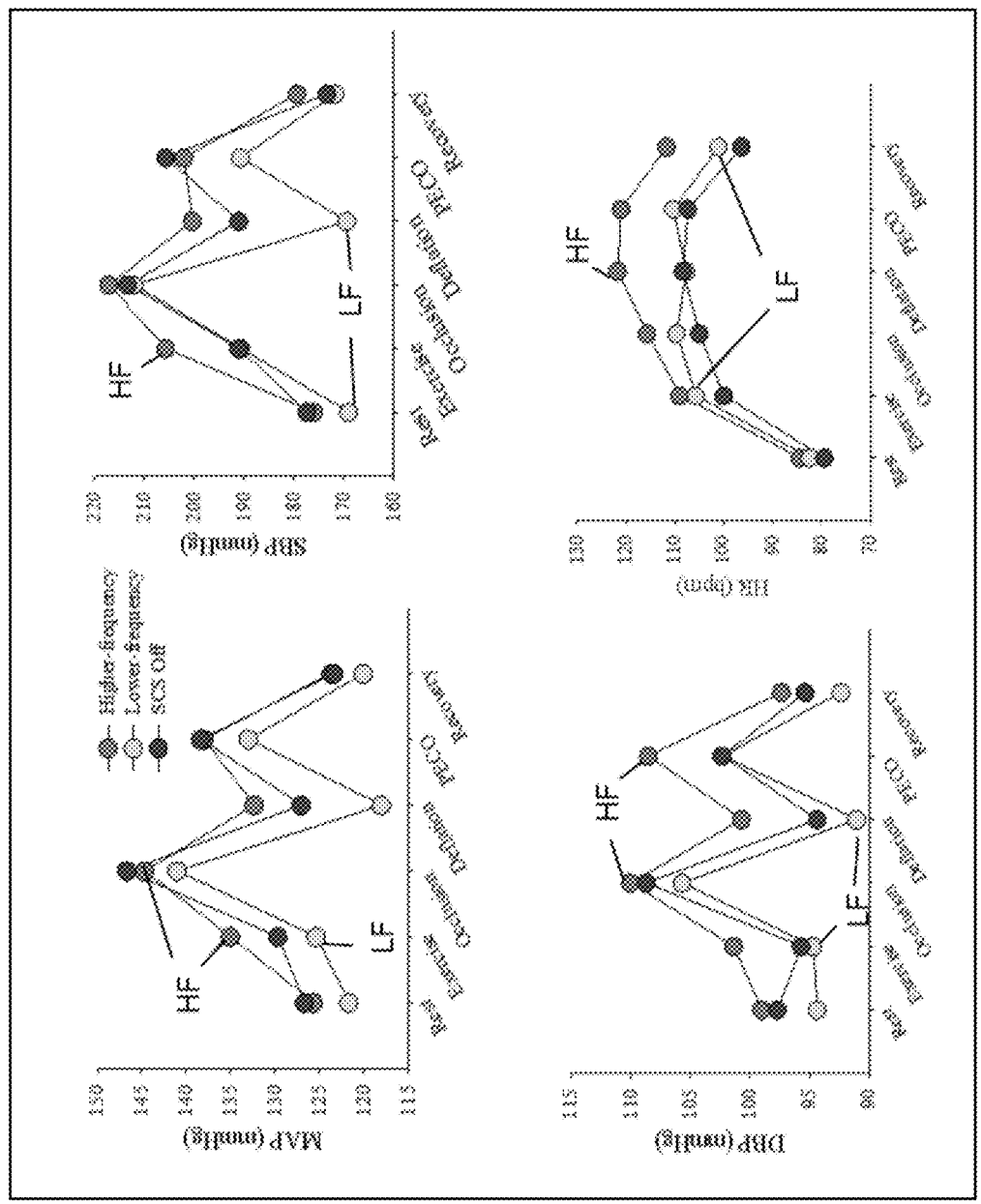
FIGS. 10-11 illustrate plots of data points for various measures taken during the experiment illustrated in FIG. 9.
Figure 11:
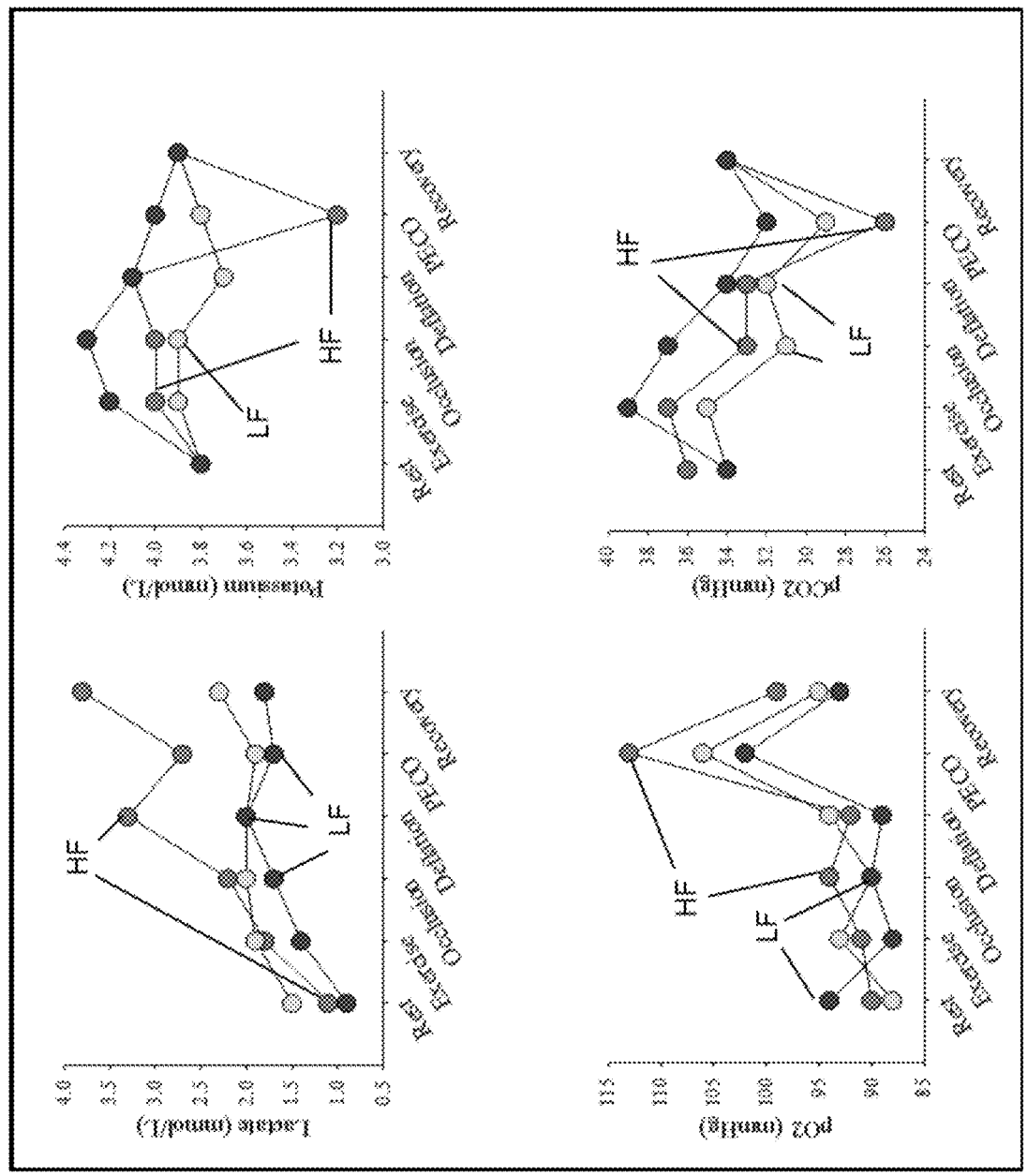

Experimental data suggests that differential blood pressure responses may be achieved by using different parameters sets. For example, the modulation of BP may depend on the frequency of SCS. FIG. 9 illustrates screening, procedures and exercise protocol for an experiment. SCS leads were inserted into the lumbar space, and guided via fluoroscopy to position the electrodes to modulate the thoracic space (T10-T12). Additionally, an arterial line was placed. The exercise protocol to evaluate the blood pressure response includes deliver SCS for 5 minutes before exercising, and then proceeding to three bouts of steady-state cycling at 30% of $VO_{2\ PEAK}$. A leg cuff was used to provide occlusion to stimulate group III/IV afferents during exercise (e.g. 80 mmHg) and post exercise (PECO: post-exercise circulatory occlusion) (e.g. 200 mmHg). Heart rate was monitored with a 12-lead ECG, continuous blood pressure was measured via the arterial line, ad blood draws via the artier line were performed to evaluate lactate, K+, $pO_2$, and $pCO_2$. The exercise protocol was performed with no SCS, SCS delivered at 100 Hz, and SCS delivered at 1000 Hz. FIGS. 10-11 illustrate the data points, taken at the arrows within the protocol illustrated in FIG. 9, for the lower frequency (LF) SCS (e.g. 100 Hz), the higher frequency (HF) SCS (e.g. 1,000 Hz), and off. The figures illustrate plots of the mean arterial pressure (MAP), systolic blood pressure (SBP), diastolic blood pressure (DBP), heart rate (HR), lactate, potassium, percent oxygen, and percent carbon dioxide.

The data suggests differential BP responses to SCS dependent on frequency. 100 Hz SCS decreased MAP with the largest decrease observed during final exercise (−9 mmHg). 1 kHz SCS increased MAP with the largest increase observed during initial exercise (+9 mmHg). 100 Hz SCS increased HR with the largest increase observed during initial exercise (+5 bpm). 1 kHz SCS increased HR with the largest increase observed during final exercise (+13 bpm). Lactate, a metabolic by-product of muscle contraction, increased with exercise, more so with 1 kHz SCS. Potassium increased throughout exercise, more so without SCS. Percent oxygen increased and percent carbon dioxide decreased with full occlusion (PECO), indicating that activation of the group III/IV afferents caused hyperventilation. The changes in pO2 and pCO2 appear to be augmented with SCS. Although the study suggests that modulation of BP may depend on the frequency of SCS, the differential modulation of BP, however, does not appear to be an effect of SCS on group III/IV skeletal muscle afferents.

Various embodiments described herein use 100 Hz to chronically maintain a lower resting BP and a 1 kHz stim to avoid orthostatic hypotension. Sensors may be used to sense when a subject is about to stand and switch from 100 to 1000 Hz stimulation. The system may include a button (or other user interface) for the patient to switch it themselves if they are feeling lightheaded or about to stand. Heart failure sensors may be used switch from 100 to 1000 if a patient is decompensating. Some embodiments may monitor for shock and make the switch.

Additional Low Blood pressure conditions that may be monitored include postural orthostatic hypotension (POTS), prolonged bed rest or standing, neurally-mediated hypotension—dizziness, nausea and fainting, decreases in blood volume such as may be attributed to trauma/shock, septic shock, ulcers/internal bleeding/dehydration. allergic reactions, heart conditions such as heart failure/acute decompensation, arrhythmia (AF), bradycardia, and medication intake such as Beta Blockers and diuretics.

As blood pressure responses may vary between patients, some embodiments may search for appropriate responses by testing different stimulation frequencies and recording blood pressure responses in different conditions over a period when the patient is at rest, is changing from prone or supine to standing, or is active (all measured with 3 axis accelerometer). The monitoring period could continue until a statistically significant BP difference is found. As a simple example, BP could be monitored across stimulation frequencies of 75 Hz, 100 Hz, 125 Hz, 750 Hz, 1000 Hz and 1250 Hz for 5 minutes each while a patient is lying in bed; then the optimal "low BP" and "high BP" settings used for subsequent therapy. This could continue throughout the course of the night with finer titrations frequency (and/or other parameters) to optimize results. The monitoring and therapy optimization may occur on an established schedule, e.g. after every 1 month or after every 1 year, to ensure optimal therapy settings are continually provided to the patient (understanding the patients' physiological responses may change with time).

While testing stimulation parameters, evoked compound action potentials and blood pressure responses may be monitored to establish an association between the action potentials and the blood pressure response. Then the measurement of action potentials may be used in a closed loop therapy to titrate therapy without measuring blood pressure. Tilt tests in a clinic or a similar protocol could be done to speed up acquisition of data for specific SCS settings. In addition to frequency, a number of additional parameters can be tested including pulse width, amplitude, duty cycle, burst stimulation, pulse shape, etc. Multiple waveforms may be overlaid and used concurrently or in an alternating fashion.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:
1. A method for controlling blood pressure in a patient, comprising:
    delivering a therapy for chronically maintaining blood pressure with a prescribed range, including delivering neuromodulation energy to neural tissue in a spinal cord or near the spinal cord using a first parameter set;
    determining an actual or anticipated blood pressure demand event indicated for a blood pressure change; and
    responding to the determined actual or anticipated blood pressure demand event by delivering neuromodulation energy using a second parameter set to change the blood pressure,
    wherein the blood pressure demand event is indicated for an increased blood pressure, delivering the therapy includes delivering spinal cord stimulation (SCS) therapy to a thoracic region of the spinal cord, and the frequency of the neuromodulation energy delivered using the first parameter set is within a range between 20 Hz to 200 Hz, and the frequency of the neuromodulation energy delivered using the second parameter set is within a range between 700 Hz to 1500 Hz.
2. The method of claim 1, wherein delivering the SCS includes delivering the SCS within a T10-T12 region.

3. The method of claim 1, wherein delivering the SCS includes delivering the SCS to cause paresthesia in legs of the patient, and the paresthesia covers a majority of both legs and is perceived by the patient as substantially uniformly distributed in the legs.

4. The method of claim 1, wherein the neuromodulation energy delivered using the first parameter set and the neuromodulation energy delivered using the second parameter set have different waveform with different pulse patterns or waveform shapes.

5. The method of claim 1, wherein delivering the therapy includes delivering neuromodulation energy to a dorsal column or to a dorsal horn, or delivering neuromodulation energy to a dorsal root ganglia (DRG) or to a dorsal root, or delivering neuromodulation energy to a sympathetic chain or to a peripheral sympathetic nerve.

6. The method of claim 1, wherein delivering the therapy includes delivering spinal cord stimulation (SCS) to a lumbar or cervical region of the spinal cord.

7. The method of claim 6, wherein delivering the therapy includes delivering SCS to at least two of a lumbar region, a thoracic region or a cervical region of the spinal cord.

8. The method of claim 1, wherein the first parameter set and the second parameter set include a different parameter value of a different range of parameter values for at least one parameter selected from a group of parameter consisting of: frequency, pulse width, burst duration for a burst of pulses, active electrodes, fractionalization values for active electrodes.

9. The method of claim 1, wherein the blood pressure demand event includes a posture change or an activity change for the patient, or the blood pressure demand event includes at least one of acute decompensation in heart failure, arrhythmia, or bradycardia, or the blood pressure demand event includes at least one of neurally-mediated hypotension, decreases in blood volume, anaphylactic shock or medication intake.

10. The method of claim 1, wherein determining the actual or anticipated blood pressure demand event includes:
sensing blood pressure to determine the blood pressure event;
sensing evoked compound action potentials associated with a blood pressure response; sensing activity;
sensing posture; or
receiving via a user interface a user inputted signal.

11. The method of claim 1, wherein the actual or the actual or anticipated blood pressure demand event includes:
a posture change;
activity change;
acute decompensation in heart failure;
arrhythmia;
bradycardia;
anaphylactic shock; or
medication intake.

12. The method of claim 1, wherein the patient has orthotic intolerance, and the actual or anticipated blood pressure demand event includes postural transitions for the patient.

13. The method of claim 1, wherein the patient has elevated exercise pressor reflex and the actual or anticipated blood pressure demand event includes dynamic blood pressure swings.

14. The method of claim 1, further comprising optimizing the first and second parameter sets to provide the desired blood pressure responses.

15. The method of claim 14, wherein optimizing the first and second parameter sets includes:

detecting blood pressure or another indicator of sympathetic tone, and using the detected blood pressure or other indicator of sympathetic tone to optimize the first and second parameter sets;
detecting paresthesia coverage in lower legs when the neuromodulation energy is delivered using the first parameter set;
optimizing at least one of the first and second parameter sets for pain relief; or
optimizing the first and second parameter sets includes optimizing neuromodulation frequencies to provide the desired blood pressure responses.

16. The method of claim 14, wherein optimizing the first and second parameter sets includes implementing an optimization schedule to determine when the first and second parameters sets are optimized.

17. A system, comprising:
a blood pressure modulation device configured to deliver a therapy to chronically maintain blood pressure within a prescribed range, the blood pressure modulation device including a neuromodulator configured to deliver neuromodulation energy to neural tissue in a spinal cord or near the spinal cord using a first parameter set; and
a controller, including analyzer circuitry configured to determine an actual or anticipated blood pressure demand event indicated for a blood pressure change, and therapy parameter adjuster circuitry configured to respond to the actual or anticipated blood pressure demand event by delivering neuromodulation energy using a second parameter set to change the blood pressure,
wherein the blood pressure demand event is indicated for an increased blood pressure, the therapy includes a spinal cord stimulation (SCS) therapy to a thoracic region of the spinal cord, and the frequency of the neuromodulation energy delivered using the first parameter set is within a range between 20 Hz to 200 Hz, and the frequency of the neuromodulation energy delivered using the second parameter set is within a range between 700 Hz to 1500 Hz.

18. The system of claim 17, wherein the actual or the actual or anticipated blood pressure demand event includes:
a posture change; activity change; acute decompensation in heart failure; arrhythmia; bradycardia; anaphylactic shock; or medication intake.

19. A non-transitory machine-readable medium including instructions, which when executed by a machine, cause the machine to deliver a therapy for chronically maintaining blood pressure with a prescribed range, including deliver neuromodulation energy to neural tissue in a spinal cord or near the spinal cord using a first parameter set, determine an actual or anticipated blood pressure demand event indicated for a blood pressure change, and respond to the determined actual or anticipated blood pressure demand event by delivering neuromodulation energy using a second parameter set to change the blood pressure,
wherein the blood pressure demand event is indicated for an increased blood pressure, the therapy includes a spinal cord stimulation (SCS) therapy to a thoracic region of the spinal cord, and the frequency of the neuromodulation energy delivered using the first parameter set is within a range between 20 Hz to 200 Hz, and the frequency of the neuromodulation energy delivered using the second parameter set is within a range between 700 Hz to 1500 Hz.

20. The non-transitory machine-readable medium of claim 19, wherein the actual or the actual or anticipated blood pressure demand event includes: a posture change; activity change; acute decompensation in heart failure; arrhythmia; bradycardia; anaphylactic shock; or medication intake.

* * * * *